United States Patent [19]

Tsunekawa et al.

[11] Patent Number: 5,169,986
[45] Date of Patent: Dec. 8, 1992

[54] ORGANIC NONLINEAR OPTICAL MATERIAL

[75] Inventors: Tetsuya Tsunekawa; Tetsuya Gotoh; Keiichi Egawa, all of Otsu, Japan

[73] Assignee: Toray Industries, Inc., Tokyo, Japan

[21] Appl. No.: 599,745

[22] Filed: Oct. 19, 1990

Related U.S. Application Data

[60] Division of Ser. No. 225,655, Jul. 25, 1988, Pat. No. 4,987,255, which is a continuation of Ser. No. 52,595, May 21, 1987, abandoned.

[30] Foreign Application Priority Data

May 21, 1986 [JP] Japan .................. 61-114486

[51] Int. Cl.$^5$ .......................................... C07C 251/04
[52] U.S. Cl. ............................... 564/273; 548/570; 549/404; 558/414; 558/422; 560/35; 562/440; 564/152; 564/153; 564/157; 564/163; 564/185; 564/212; 564/213; 564/272; 564/274
[58] Field of Search .................. 548/570; 549/404; 558/414, 422; 560/35; 562/440; 564/152, 153, 157, 163, 185, 212, 213, 220, 272, 273, 274

[56] References Cited

U.S. PATENT DOCUMENTS

| | | | |
|---|---|---|---|
| 3,592,913 | 7/1971 | Fujinami et al. | 564/272 X |
| 3,827,780 | 8/1974 | Labes | 564/273 X |
| 4,047,803 | 9/1977 | Yaguchi et al. | 564/273 X |
| 4,122,026 | 10/1978 | Osman | 564/273 X |
| 4,622,409 | 11/1986 | Nicoud et al. | 548/570 |
| 4,733,109 | 3/1988 | Palazzotto | 307/427 |
| 4,987,255 | 1/1991 | Tsunekawa et al. | 564/119 |

FOREIGN PATENT DOCUMENTS

| | | |
|---|---|---|
| 44-10775 | 5/1969 | Japan . |
| 44-20740 | 9/1969 | Japan ................. 564/272 |
| 59-21665 | 2/1984 | Japan . |

OTHER PUBLICATIONS

ACS, Symposium Series, 233 (1983).
D. J. Williams, Chem. Int. Ed. Engl. 23, p. 690, (1984).
V. D. Shigorin, "Materials and Apparatus in Quantum Radio Physics", p. 77 (1982).
Al-Tai et al., "Nuclear . . . ", J. Chem. Soc. Perkin II, 1976, pp. 133–136.
Kozlov et al (Chem. Abs., 71:12748d (1969).
Chem. Abstract No. 133601q, vol. 87 (1977).
Williams, "Organische Polymere und . . . ", Angewandte Chemie, vol. 96, 1984, pp. 637–651.
Chem. Abstract No. 69147j, vol. 83 (1975).

Primary Examiner—Richard L. Raymond
Attorney, Agent, or Firm—Birch, Stewart, Kolasch & Birch

[57] ABSTRACT

The present invention provides an organic nonlinear optical material including a benzylidene-aniline derivative having an electron-donating substituent introduced at the 4-position and an electron-accepting substituent introduced at the 4'-position, by selecting as the conjugated $\pi$ electronic system a benzylidene-aniline derivative having a large molelcular hyperpolarizability and yet a dipole moment as small as those of benzene derivatives, and introducing a molecular alignment-regulating substituent. The centrosymmetry in the bulk state of the material, for example, in the crystal state, is destroyed and the molecular alignment is regulated to such a bulk structure so that the optical nonlinearity possessed by the molecule is effectively utilized. The material exhibit a large optical nonlinearity never attained by conventional techniques.

the intermolecular cohesive force due to the $\pi$ electron interaction between the molecules in the present invention is larger than that between a benzene derivative. Consequently, the material has, comparatively, a high melting point, a low subliming property, and a low water-absorbing property. In conclusion, a practically invaluable nonlinear optical material having a high durability in the bulk state and an excellent resistance to laser damage is provided.

9 Claims, 9 Drawing Sheets

ORGANIC NONLINEAR OPTICAL MATERIAL

This application is a continuation of copending application Ser. No. 07/225,655 filed on Jul. 25, 1988, now U.S. Pat. No. 4,987,255, which was a continuation application of Ser. No. 07/052,595 filed on May 21, 1987, now abandoned.

BACKGROUND OF THE INVENTION

1. Field of the Invention

The present invention relates to an organic nonlinear optical material to be used for optical information processing or optical communication. More particularly, the present invention relates to an organic compound having a large optical nonlinearity, excellent resistance to laser damage, and high durability.

2. Description of the Related Art In the field of optoelectronics, research is being conducted to develop a material having an outstanding nonlinear optical effect never attained by existing materials and the capability of a high speed response, to realize a nonlinear optical element having an extremely high performance.

The foregoing research has been concentrated mainly on inorganic materials, but a material satisfying the above requirements has not yet been found. Recently, an organic compound having a conjugated $\pi$ electronic system expected to have a large nonlinear optical effect and a high speed response in principle has, therefore, attracted much attention in the art.

With reference to organic materials having the second order optical nonlinearity, various types of compounds have been examined, and many disclosures of such materials have been made [(1) ACS, Symposium Series, 233 (1983) and (2) D. J. Williams Angew, Chem. Int. Ed. Engl. 23, p 690 (1984)].

For example, there can be mentioned benzene and pyridine derivatives such as N-(4-nitrophenyl)-L-prolinol (NPP) (Japanese Unexamined Patent Publication No. 59-21665 and U.S. Pat. No. 4,622,409), N-[5-(nitropyridyl)]-L-prolinol (PNP) and 2-acetylamino-4-nitro-N,N-dimethylaniline (DAN), stilbene derivatives such as 4-dimethylamino-4'-nitrostilbene (DANS), stilbazoliums such as 4'-dimethylamino-N-methyl-4-stilbazolium methosulfate (DMSM), and benzylidene-aniline derivatives such as 4'-nitrobenzylidene-4-(N,N-dimethyl)aniline, 4'-nitrobenzylidene-4-methylaniline [Proceedings (Trudy) of the P. N. Levedeb Physics Institute, Vol. 98 (1982), Basov, N. G. Editor (Consultants Bureau: New York, NY), Shigorin, V. D. p 77: "Materials and Apparatus in Quantum Radio Physics"),] and 4'-methylbenzylidene-4-nitroaniline.

It is believed that the optical nonlinearity of an organic compound having a conjugated $\pi$ electronic system is considered to be due to fluctuations of $\pi$ electrons responding to an applied optical electric field. There has been a guiding principle in designing organic nonlinear optical molecules, that is, electron-donating and electron-accepting substituents are introduced into conjugated $\pi$ electronic systems as in the above-mentioned known compound's.

In general, the crystal structure of an organic compound is determined by the structures of respective molecules. More specifically, hydrogen bonding at the time of molecular packing, and intermolecular cohesive forces such as the van der Waals interaction and the dipole-dipole interaction determines the crystal structure in the balance of these forces.

If a highly electron-donating or electronaccepting substituent such as an amino group or a nitro group is introduced, the dipole moment possessed by the molecule is increased and the dipole-dipole interaction becomes strong upon formation of a crystal.

This strong dipole-dipole interaction among molecules according to the above-mentioned guiding principle of molecular design, that is, compounds having electron-donating and electron-accepting substituents in the conjugated $\pi$ electronic system, causes formation of a centrosymmetric crystal having a structure in which dipoles of two molecules negate each other.

In this centrosymmetric crystal, contrary to our wishes, the second order optical nonlinearity is not manifested.

There can be seen a contrivance in a molecular design in the disclosed works that an optically active substituent or a substituent having a large hydrogen bond-forming capacity is introduced into the conjugated x electronic system to destroy the centrosymmetry of the crystal, which hinders realization of the macroscopic optical nonlinearity in the crystalline state. There are examples of success, but those are limited to benzene derivatives and pyridine derivatives.

Typical instances are NPP, PNP, and DAN, but they fail to have such a large nonlinearity that enables a nonlinear optical element having a desired novel function to be realized.

This is thought to be because the molecular hyperpolarizability, which is an important factor in producing a molecular crystal having a sufficiently large nonlinearity for a practical use, is small in benzene derivatives and in pyridine derivatives.

As the properties that should be possessed by nonlinear optical materials, there can be mentioned a large optical nonlinearity, a high speed optical response, a high transparency to laser beams, a high resistance to laser damage, phase matching characteristics, good crystal growth characteristics, high mechanical strength, and a high processability.

NPP and PNP are not satisfactory in terms of crystal growth characteristics in the melt phase or in the gas phase and have problems in that their durabilities are not sufficient because of their hygroscopicity or photodegradation properties. DAN is also defective in the durability because of its hygroscopicity or sublimation property.

A class of compounds such as stilbene derivatives and benzylidene aniline derivatives having an elongated conjugated $\pi$ electronic system in the main skeleton and an increased second order molecular hyperpolarizability, larger than 10 times that of the benzene derivatives such as p-nitroaniline, show only a macroscopic optical nonlinearity in the crystals smaller than those of the benzene derivatives since their dipole moments are accordingly increased and the crystals become centrosymmetric or even in the cases the crystals are noncentrosymmetric molecular alignments are not optimized.

· Therefore, the introduction of a quaternary ammonium structure having a large steric hindrance is now under examination as a means of destroying the centrosymmetry of the crystal. A typical instance is DMSM manifesting a relatively large optical nonlinearity because of a large molecular hyperpolarizability and a noncentrosymmetric crystal structure. However, compounds of this type are unsatisfactory in terms of durability and processability because of the hygroscopicity and an easy structural change of crystal such as polymorphism is readily caused due to the quaternary ammonium structure.

As is apparent from the foregoing description, if only molecular decoration according to the conventional guiding principle of the molecular design is attempted, it is difficult to provide a nonlinear optical material exhibiting a large optical nonlinearity in the bulk state such as a crystal and satisfying the requirements indispensable for practical use.

SUMMARY OF THE INVENTION

It is a primary object of the present invention to solve the problems of the conventional techniques and provide a practically valuable organic nonlinear optical material having a large optical nonlinearity and an improved resistance to laser damage.

As pointed out hereinbefore, it is considered that the appearance of centrosymmetry of a crystal greatly depends on the strength of the dipole-dipole interaction. Accordingly, it was thought that molecular decoration of the compound having a $\pi$ skeleton, in which the dipole moment of the molecule is small and the centrosymmetry of the crystal is readily destroyed, would be effective.

As a result of quantum chemical calculation, the present inventors found that a benzylidene-aniline derivative in which a benzene ring having an electrondonating substituent introduced therein is located on the N side of the —N=CR—linkage, has a large molecular hyperpolarizability because of a long conjugated $\pi$ electronic system, and moreover the derivative has a polarization, that is, a dipole moment, in the ground state as small as those of benzene derivatives because of a large electronegativity of the nitrogen atom.

The present inventors actually introduced a molecular alignment-regulating substituent to the derivative on the basis of the above finding, and found that the derivative in a crystalline state could show such a large optical nonlinearlity that could not be ever attained by the conventional techniques. The present invention was thus completed on this basis.

In accordance with the present invention, the foregoing object is attained by an organic nonlinear optical material comprising a benzylidene-aniline derivative having an electron-donating substituent (D) at the 4-position, an electron-accepting substituent (A) at the 4'-position, and at least one substituent having a function of regulating the molecular alignment in the crystal at any substitutable position, and having a nonlinearity at least 10 times that of urea.

DESCRIPTION OF THE PREFERRED EMBODIMENTS

Figure 1:
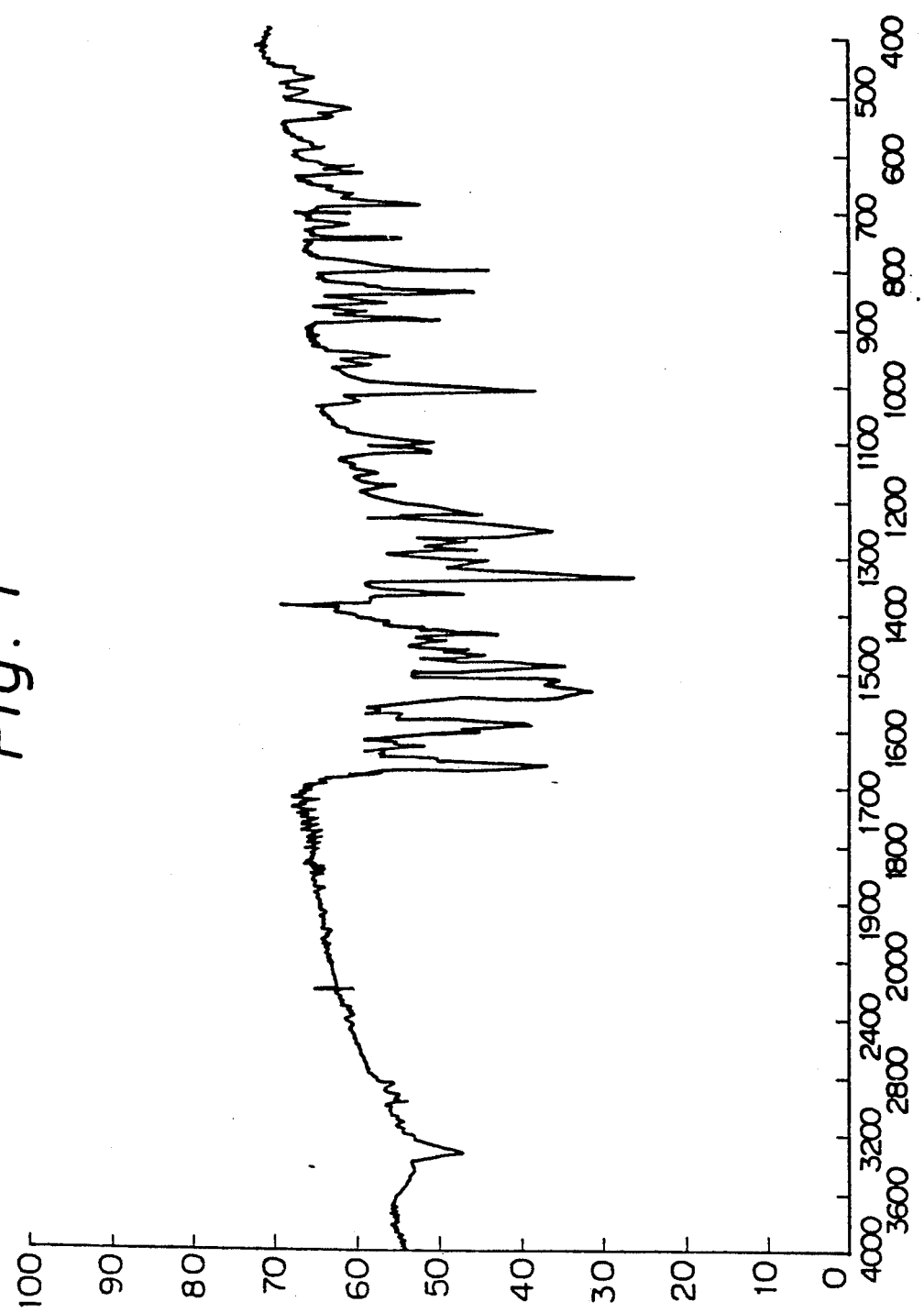
FIGS. 1 through 6 are infrared absorption spectrum charts of compounds obtained in examples of the present invention; and, FIGS. 7 through 9 are infrared absorption spectrum charts of compounds obtained in the comparative examples.

As pointed out hereinbefore, the appearance of centrosymmetry of a crystal greatly depends on the strength of the dipole-dipole interaction among molecules. Therefore, it was considered that the molecular decoration of a compound having a $\pi$ skeleton, in which the dipole moment of the molecule is small and the centrosymmetry of the crystal is readily destroyed, would be effective.

As a result of quantum chemical calculation, we found that a benzylidene-aniline derivative (represented by the following formula [3]) in which a benzene ring having an electron-donating substituent introduced therein is located on the N side of the —N=CR—linkage has a large molecular hyperpolarizability because of a long conjugated $\pi$ electronic system, and moreover the derivative has a polarization in the ground state, that is, a dipole moment, as small as those of benzene derivatives because of a large electronegativity of the nitrogen atom. As examples are shown in comparative examples 5 and 6, benzylidene-aniline derivatives having exclusively electron-donating and electron-accepting groups did not show large optical nonlinearities. A molecular alignment-regulating substituent was thereby introduced to the above type of benzylideneaniline derivative on the basis of the result of quantum chemical calculation, and it was confirmed that a large optical nonlinearity never attained by the conventional techniques could be manifested. The present invention was completed on this basis.

In the present invention, a benzylidene-aniline derivative having a structure represented by the following formula [3] has at least one substituent having a function of regulating the molecular alignment in the crystal:

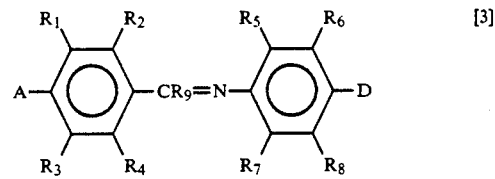

wherein D stands for an electron-donating substituent, A stands for an electron-accepting substituent, and $R_1$ through $R_9$ stand for a molecular alignment-regulating substituent.

The characteristic of the present invention is that the centrosymmetry in a bulk state, for example, in a crystalline state, is destroyed and the molecular alignment is regulated to such a bulk structure in that the nonlinearity possessed by the molecule can be really utilized, whereby a large optical nonlinearity never attainted by the conventional techniques can be manifested by the following two contrivances:

(1) selecting as the conjugated $\pi$ electronic system a benzylidene-aniline derivative having a large molecular hyperpolarizability and yet a dipole moment as small as those of benzene derivatives, and (2) introducing a molecular alignment-regulating substituent.

Moreover, as the intermolecular cohesive force between the molecules in the present invention is generally larger than that between benzene derivatives by dint of the increased $\pi$ electronic interaction, the benzylidene-aniline derivative of the present invention has comparatively a high melting point, a low subliming property, and a low water-absorbing property, and has high durability in the bulk state. Results shown in Table 4 proved a low water absorbing property of the benzylidene-aniline derivative in this invention.

Of organic nonlinear optical materials included within the scope of the present invention, even a material not having a tremendously large optical nonlinearity, which is comparable to those of the known benzene derivatives, can be used practically while utilizing a high durability and a high-speed optical response inherent to organic materials, if the urea ratio of the optical nonlinearity is at least about 10, that is, if the optical nonlinearity is almost equal to those of inorganic materials such as lithium niobate.

It should be emphasized that the organic nonlinear optical materials included within the scope of the present invention having an optical nonlinearity at least 150 times that of urea is especially important, because a nonlinear optical element never realized by the conventional techniques can be constructed with the materials.

A compound especially preferred in the present invention is a benzylidene-aniline derivative in which a substituent having a function of regulating the molecular alignment in the crystal is present in at least one of the positions of $R_1$ through $R_9$ in the following formula [1]:

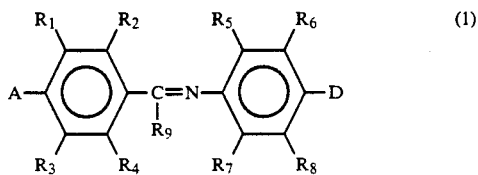

wherein D stands for an electron-donating substituent, A stands for an electron-accepting substituent, and $R_1$ through $R_9$ stand for a hydrogen atom or an optional substituent and at least one of $R_1$ through $R_9$ is a substituent having a function of regulating the molecular alignment.

The substituent having a function of regulating the molecular alignment in the formula [1] is the substituent which regulates the alignment of nonlinear optical molecules in the bulk state so as to attain a large macroscopic optical nonlinearity. Accordingly, this denotes a substituent which can introduce an intermolecular force capable of changing the bulk structure as the result of the molecular packing or a substituent capable of lowering the symmetry of the molecules. Since a substituent having a high hydrogen bonding forming property or a large steric hindrance has a large force for changing the packing, such substituent is especially effective as the molecular alignment regulating substituent referred to in the present invention.

As typical instances of the molecular alignment regulating substituent, there can be mentioned alkanoylamino groups such as acetylamino, ethylcarbonylamino and t-butylcarbonylamino groups, phenylcarbonylamino groups such as benzoylamino and p-acetylaminophenylcarbonylamino groups, and substituents formed by partially halogenating the foregoing substituents. Examples of success are shown in Examples 1, 2, 3, 4, and 5.

The substituent ordinarily means a group having one binding position, but the molecular alignment-regulating substituent referred to in the present invention includes a substituent having a plurality of binding positions and a substituent having binding positions in at least two molecules. Accordingly, a substituent connecting a plurality of molecules is included.

For example, there can be mentioned a substituent connecting two molecules of benzylidene-aniline through an amide linkage that is introduced by the use of an acid dichloride such as oxalyl chloride, malonyl chloride, succinyl chloride, phthaloyl chloride or terephthaloyl chloride.

The molecular alignment-regulating substituent $R_9$ in the formula [1] is specially related to the coplanarity of the two aromatic rings, through the imine bond (—CR=N—) that is, the amplitude of spontaneous polarization in the conjugated $\pi$ electronic system. Accordingly, a substituent having a relatively small steric hindrance is preferable in order to maintain the large molecular hyperpolarizability and manifest a large optical nonlinearity. Therefore, a substituent composed of 1 to 5 carbon atoms or hydrogen is effective. Hydrogen is particularly preferred, and in this case, synthesis is relatively easy to be accomplished.

As examples of the substituent, there can be mentioned saturated and unsaturated alkyl groups such as methyl, ethyl, propyl, 2-propenyl and 2-butenyl groups, hydroxyalkyl groups such as hydroxymethyl, 2-hydroxyethyl and 3-hydroxypropyl groups, alkoxyalkyl groups such as 2-methoxyethyl and 3-ethoxypropyl groups, halogenoalkyl groups such as 2-chloroethyl and 5-bromopentyl groups, carboxyalkyl groups such as 2-carboxyethyl and 3-carboxypropyl groups, and alkoxycarbonylalkyl groups such as 2-ethoxycarbonylethyl and 4-methoxycarbonylbutyl groups.

In order to prevent reduction of the optical nonlinearity by reduction of the molecule density per unit volume in optimizing the molecular packing for manifesting the optical nonlinearity, it is preferable that the number of the molecular alignment-regulating substituents $R_1$ through $R_8$ is as small as possible. Hence, the seven substituents of $R_1$ through $R_8$ are preferably hydrogen atoms.

In the present invention, it was also found that a large optical nonlinearity can be manifested only by introducing one molecular alignment-regulating substituent into the benzene ring having an electrondonating substituent. In this case, an especially high effect is attained when the molecular alignment regulating substituent is introduced to the orthoposition to the electron-donating substituent.

As typical instances of the substituent to be introduced, there can be mentioned the acetylamino, halogenoacetylamino, and benzoylamino groups.

The compound of the present invention can be obtained through an ordinary imine compound synthesis procedure in which a carbonyl compound and an amine are mixed and condensed in an alcohol or benzene in the presence of a Lewis acid as a catalyst [M. M. Sprung, Chem. Rev., 26, 297 (1940)].

As the electron-donating substituent referred to in the present invention, there can be mentioned amino groups such as amino, monomethylamino, dimethylamino, diethylamino, n-butylamino, and t-butylamino groups, optically active amino groups such as L-(2-hydroxymethyl)-pyrolidinyl, L-alaninyl, L-serinyl, and L-tyrosinyl groups, a hyroxyl groups, alkoxy groups such as methoxy, ethoxy, and n-butoxy groups, linear and branched alkyl groups such as methyl, ethyl, n-propyl, n-butyl, t-butyl, n-pentyl, and n-octadecyl groups, hydroxyalkyl groups such as hydroxymethyl and hydroxyethyl groups, and halogen atoms. As the electron-accepting substituent, there can be mentioned a nitro group, a cyano group, an isocyanato group, a formyl group, alkoxycarbonyl groups such as methyl carboxylate and ethyl carboxylate groups, a sulfonyl group, and halogen atoms.

A halogen has both electron-donating and electronaccepting properties, and therefore, can be introduced as either an electron-donating substituent or an electron-accepting substituent.

Introduction of a nitro group as the electronaccepting substituent is especially preferable to improve the optical nonlinearity of the compound.

Introduction of substituents into positions other than the positions where the electron-donating, electron-accepting, and molecular alignment-regulating substituents are introduced in the benzylidene-aniline basic skeleton is not particularly critical, but if any substituent is introduced, the substituent must not have a significant influence on the conjugated $\pi$ electronic system or the function of the molecular alignment regulating substituent.

A compound comprising a combination of a weak electron-donating substituent and a strong electronaccepting substituent, or a combination of a strong electron-donating substituent and a weak electronaccepting substituent, is preferable to realize the noncentrosymmetry easily in the crystal formed by the compound and to prevent a reduction of manifestation of the nonlinear optical effect due to absorption by shifting the adsorption of the compound to a relatively shorter wave length, although the optical nonlinearity of the molecule per se is decreased.

As the weak electron-donating substituent is a combination of a weak electron-donating substituent and a strong electron-accepting substituent being introduced into the main skeleton, a substituent having a Hammett substituent constant op in the range of $0 > \sigma p > -0.4$ or a halogen is used. For example, an alkyl group such as methyl, ethyl, n-butyl, or t-butyl, a hydroxyalkyl group such as a hydroxymethyl or hydroxyethyl group, a hydroxyl group, or an alkoxy group such as a methoxy or ethoxy group is used. As the strong electron-accepting group, a substituent having a Hammett substituent constant op in the range of $\rho p > +0.5$ is used, such as a nitro or cyano group.

In this case, if a hydroxyl group or an alkoxy group is used as the electron-donating substituent, an unexpectedly large optical nonlinearity from the strength of the electron-donating property of the substituent can be obtained. Thus, these substituents are especially preferable to the present purpose.

As the strong electron-donating substituent in a combination of a strong electron-donating substituent and a weak electron-accepting substituent being introduced in the main skeleton, a substituent having a Hammett substitution constant $\sigma p$ in the range of $\sigma p \leq$ about $-0.4$ is used. For example, an amino group such as monomethylamino, dimethylamino, diethylamino, n-butylamino or t-butylamino group, or an optically active amino group such as an L-(2-hydroxymethyl)pyrolidinyl, L-alaninyl, L-serinyl or L-tyrosinyl group is used. As the weak electron-accepting substituent, there can be mentioned a substituent having a Hammett substituent constant op in the range of $0 \leq \sigma p \leq 0.5$ or a halogen, for example, a formyl group, a carbonyl group, an alkoxycarbonyl group wherein the alkoxy group is methoxy, ethoxy or t-butoxy group, or an acetoamino group.

Deuteration of the compound is effective in increasing the transparency in the near infrared region, and the deuterated compound shows the same nonlinear optical effect as that of the non-deuterated compound. Accordingly, the present invention includes the nonlinear optical compound partially or completely deuterated.

As an another type of the compound in the present invention, there is mentioned a benzylidene-aniline derivative having a structure (represented by the following formula [2]) in which a substituent having both a function of regulating the molecular alignment in the crystal and an electron-donating property is introduced at the position of D':

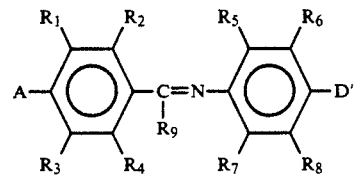

[2]

wherein D' stands for an electron-donating and molecular alignment-regulating substituent, A stands for an electron-accepting substituent, and $R_1$ through $R_9$ stand for a hydrogen atom or an optional substituent.

In the formula [2], the electron-donating and molecular alignment-regulating substituent is preferably a group —OR in which R stands for an alkyl group, an allyl group, an aryl group, an aralkyl group or a derivative thereof, since the molecular packing property thereof is excellent.

An example of this type is shown in Example 6, wherein D' is a part of ethylenedioxy group which is considered to be both an electron-donating substituent and a molecular alignment-regulating group.

A high resistance to laser damage is an important property requested to a nonlinear optical material. The detailer mechanism of laser damage is still a subject to be studies. However, the materials in this invention showed a high resistance to laser damage as the results are shown in Table 3.

It is considered that the strong $\pi$ interaction between molecules in the present invention may be one of the reasons.

The compound of the present invention is preferably used in the form of a bulk single crystal or a thin film single crystal. As the process for the preparation of the single crystal, there can be adopted a solution process, a gas phase process, and a fusion process. For example, in the case of the 4'-nitrobenzylidene-3-acetylamino-4-methoxyaniline of Example 1, a bulk single crystal can be prepared by the solution process as shown in Example 1. Moreover, a thin film single crystal can be prepared by a melt and cool process on a substrate, or by the gas phase growth technique such as vapor deposition or sublimation onto a substrate.

The so-prepared bulk single crystal or thin film single crystal is effectively utilized in manufacturing the nonlinear optical elements such as a frequency converter, a parametric oscillator, and an optical switch, and various types of the nonlinear optical devices comprising these elements.

EFFECT OF THE INVENTION

The present invention provides an organic nonlinear optical material comprising a benzylidene-aniline derivative having an electron-donating substituent introduced at the 4-position and an electron-accepting substituent introduced at the 4'-position, by (1) selecting as the conjugated $\pi$ electronic system a benzylidene-aniline derivative having a large molecular hyperpolarizability and yet a dipole moment as small as those of benzene derivatives, and by (2) introducing a molecular alignment-regulating substituent. The centrosymmetry in the bulk state of the material, for example, in a crystal, is destroyed, and the molecular alignment is regulated to such a bulk structure in that the optical nonlinearity possessed by the molecule is effectively utilized. Thus, a large optical nonlinearity never attained by the conventional techniques can be manifested with this material.

The intermolecular cohesive force due to the π electron interaction between the molecules in the present invention is larger than that between a benzene derivative. Consequently, the benzylidene-aniline derivative in the present invention has, comparatively, a high melting point, a low subliming property, and a low water-absorbing property. Therefore, a practical, invaluable nonlinear optical material having a high durability in the bulk state and an excellent resistance to laser damage can be provided.

The present invention will now be described in detail with reference to the following examples that by no means limit the scope of the invention.

EXAMPLE 1

4'-Nitrobenzylidene-3-acetylamino-4-methoxyaniline (MNBA)

(Synthesis 1)

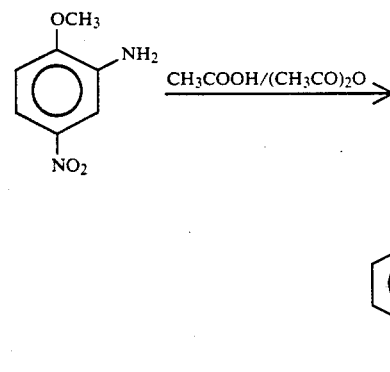

A 200 ml three-necked flask provided with a reflux condenser and a magnetic stirrer was charged with about 30 ml of an acetic acid/acetic anhydride (1/1) mixture and 8.40 g (50 millimoles) of 2-amino-4-nitroanisole, and the mixture was stirred at room temperature for about 5 hours.

After confirmation of completion of the reaction by thin layer chromatography, the reaction solution was dropped into cold water. The light yellow crude crystal thus obtained was dried in vacuum with heating to give 9.83 g of the intended compound. The yield was 93.5%.

(Synthesis 2)

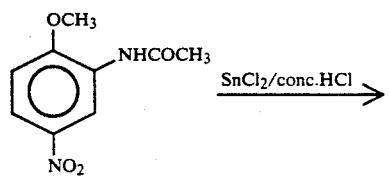

-continued

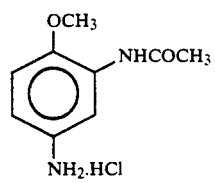

In about 30 cc of concentrated hydrochloric acid was dissolved 20.2 g (90 millimoles) of tin chloride dihydrate, and 6.31 g (30 millimoles) of 4-nitro-2-acetylaminoanisole was added to the solution with vigorous stirring and the stirring was continued during the reaction.

The initial yellow color of the reaction solution was changed to a light pink color with the generation of heat.

After about 2 hours, the light pink reaction solution was filtered and the residue was washed with cold water to obtain a white crude crystal. The crystal was vacuum-dried to obtain 2.71 g of the intended compound. The yield was 41.7%.

(Synthesis 3)

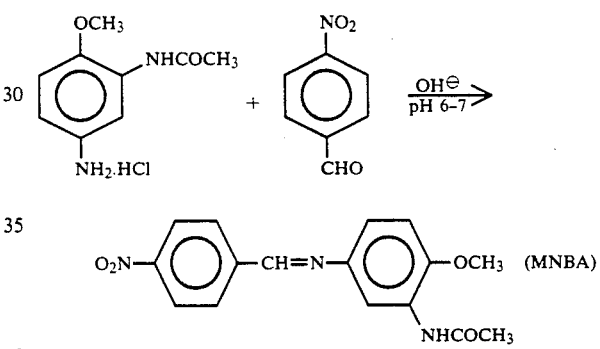

A 200 ml three-necked flask equipped with a reflux condenser and a magnetic stirrer was charged with 2.16 g (10 millimoles) of 3-acetylamino-4-methoxyaniline hydrochloride and 1.56 g (10 millimoles) of p-nitrobenzaldehyde, and the mixture was stirred at room temperature for about 10 minutes by using about 60 ml of ethanol/water (2/1) as the reaction solvent.

Then, an aqueous solution of sodium hydroxide was gradually added to the reaction mixture until the pH value became between 6 and 7, whereby the color of the reaction solution was changed to a brownish yellow color. The reaction solution was further stirred at room temperature for about 3 hours.

After confirmation of completion of the reaction by thin layer chromatography using chloroform as the developing solvent, stirring was stopped. The precipitated crude product was collected and washed with cold water.

The obtained brownish yellow crude product was dissolved in acetone and insoluble substances were removed, and the solvent was removed by a rotary evaporator to obtain a yellowish orange crude crystal.

The crude crystal was recrystallized from a chloroform/benzene (½) mixed solvent to obtain a yellow crystal. The crystal was collected and vacuum dried to obtain 1.75 g of the intended compound (MNBA). The yield was 56.0%. The melting point was 196 to 197° C.

The MNBA turned out to form a thermotropic liquid crystal by cooling from its molten state. Identification was performed by IR and elementary analysis (See Table 1 and the spectal chart of FIG. 1).

In order to examine the optical nonlinearity and the resistance to laser damage of this compound, the second harmonic generation (SHG) was measured by the powder method [S. K. Kurtz, T. T. Perry, J. Appl. Phys., 39, 3798 (1966)]. An Nd:YAG laser was used as the light source for the measurement, and the sample was pulverized to a size smaller than 10 $\mu$m in diameter by milling and then used for the measurement.

It is noted that the resistance to laser damage was evaluated based on a reduction of the SHG intensity caused by a pulsed laser with a pulse width of 200 nsec, a repetition frequency of 10 kHz, a peak power density of 9.1 $MW/cm^2$, or by a continuous oscillating laser with an average power density of 16 $kW/cm^2$.

The results of SHG measurement are shown in Table 2 and the results of evaluation of the resistance to laser damage are shown in Table 3. The MNBA according to the present invention had a large unknown optical nonlinearity of 233 times that of urea which is a common standard known compound, and had a relatively high resistance to laser damage.

When the water-solubility was examined, it was found that the MNBA according to the present invention was partically insoluble in water (see Table 4).

EXAMPLE 2

4'-Nitrobenzylidene-3-bromoacetylamino-4-methoxyaniline (MNBA-Br)

(Synthesis 1)

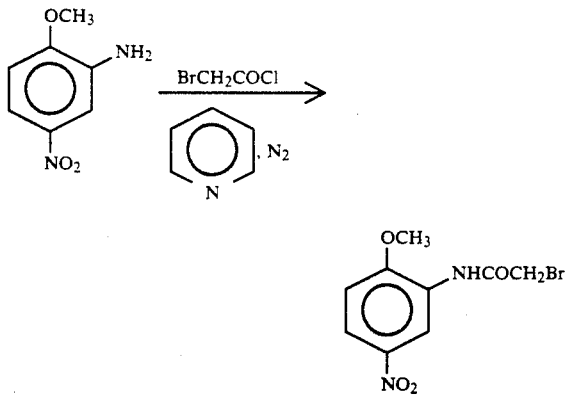

A 500 ml three-necked flask equipped with a reflux condenser, a nitrogen-inlet tube and a dropping funnel was charged with about 200 ml of dichloroethane, 16.8 g (100 millimoles) of 2-amino-4-nitroanisole and 2.4 ml of pyridine, and the mixture was stirred by means of a magnetic stirrer at room temperature for about 10 minutes under a nitrogen atmosphere.

The reaction solution was cooled in ice water and a solution of 15.8 g of bromoacetyl chloride in about 100 ml of dichloroethane was added to the solution over a period of about 15 minutes through the dropping funnel. The orange color of the reaction solution changed quickly to a light yellow color.

The temperature of the reaction solution was elevated to room temperature, and further, to about 50° C., and stirring was conducted for about 5 hours.

After confirmation of completion of the reaction by thin layer chromatography, the reaction solution was transferred into a separating funnel and about 300 ml of chloroform was added to dissolve the precipitated crystal completely, and the solution was sufficiently washed with about 1N diluted hydrochloric acid and dried on anhydrous sodium sulfate. Then, the solvent was removed by using a rotary evaporator to obtain a light yellow crude crystal of 2-bromoacetylamino-4-nitroanisole. The crude crystal was dried in vacuum with heating to obtain 25 g of the intended compound. The yield was 86.5%.

(Synthesis 2)

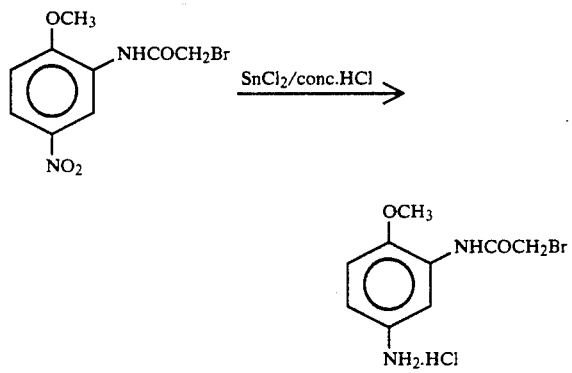

In about 40 cc of concentrated hydrochloric acid was dissolved 36.2 g (160 millimoles) of tin chloride dihydrate, 14.5 g (50 millimoles) of 2-bromoacetylamino-4-nitroanisole was added to the solution with violent stirring, and the mixture was stirred at room temperature.

The yellow reaction solution became substantially colorless with the generation of heat.

After about 2 hours, the reaction solution was directly filtered, and the residue was washed with a small amount of concentrated hydrochloric acid to obtain a white crude crystal of 3-bromoacetylamino-4-methoxyaniline hydrochloride. The crystal was vacuum dried to obtain 5.6 g of the intended compound. The yield was 38.0%.

(Synthesis 3)

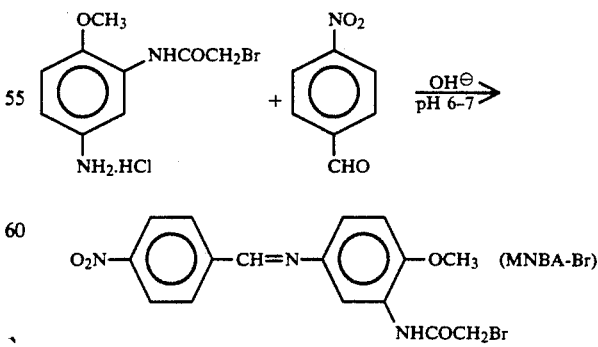

A 200 ml three-necked flask equipped with a reflux condenser and a magnetic stirrer was charged with 2.96 g (10 millimoles) of 3-bromoacetylamino-4-methoxyaniline hydrochloride, 1.51 g (10 millimoles) of p-nitrobenzaldehyde and about 60 ml of ethanol/water (2/1), and the mixture was stirred at room temperature for about 10 minutes.

Then, an aqueous solution of sodium hydroxide was gradually added to the reaction mixture until the pH value became between 6 and 7, whereby the color of the reaction solution was changed to a brownish yellow color and a precipitate was formed. Then, stirring was further continued at room temperature for about 3 hours.

After confirmation of completion of the reaction by the thin layer chromatography using chloroform as the developing solvent, stirring was stopped, and the precipitated crude product was collected and washed with cold ethanol.

The so-obtained brownish yellow crude product was dissolved in acetone and insoluble substances were removed, and the solvent was removed by a rotary evaporator to obtain a yellowish orange crude crystal.

Recrystallization of the crude crystal from a chloroform/benzene (½) mixed solvent gave a yellow crystal of 4'-nitrobenzylidene-3-bromoacetylamino-4-methoxyaniline (MNBA-Br). The crystal was collected and vacuum-dried to obtain 1.88 g of the intended compound. The yield was 48.0%. The melting point was 185 to 187° C.

Figure 2:
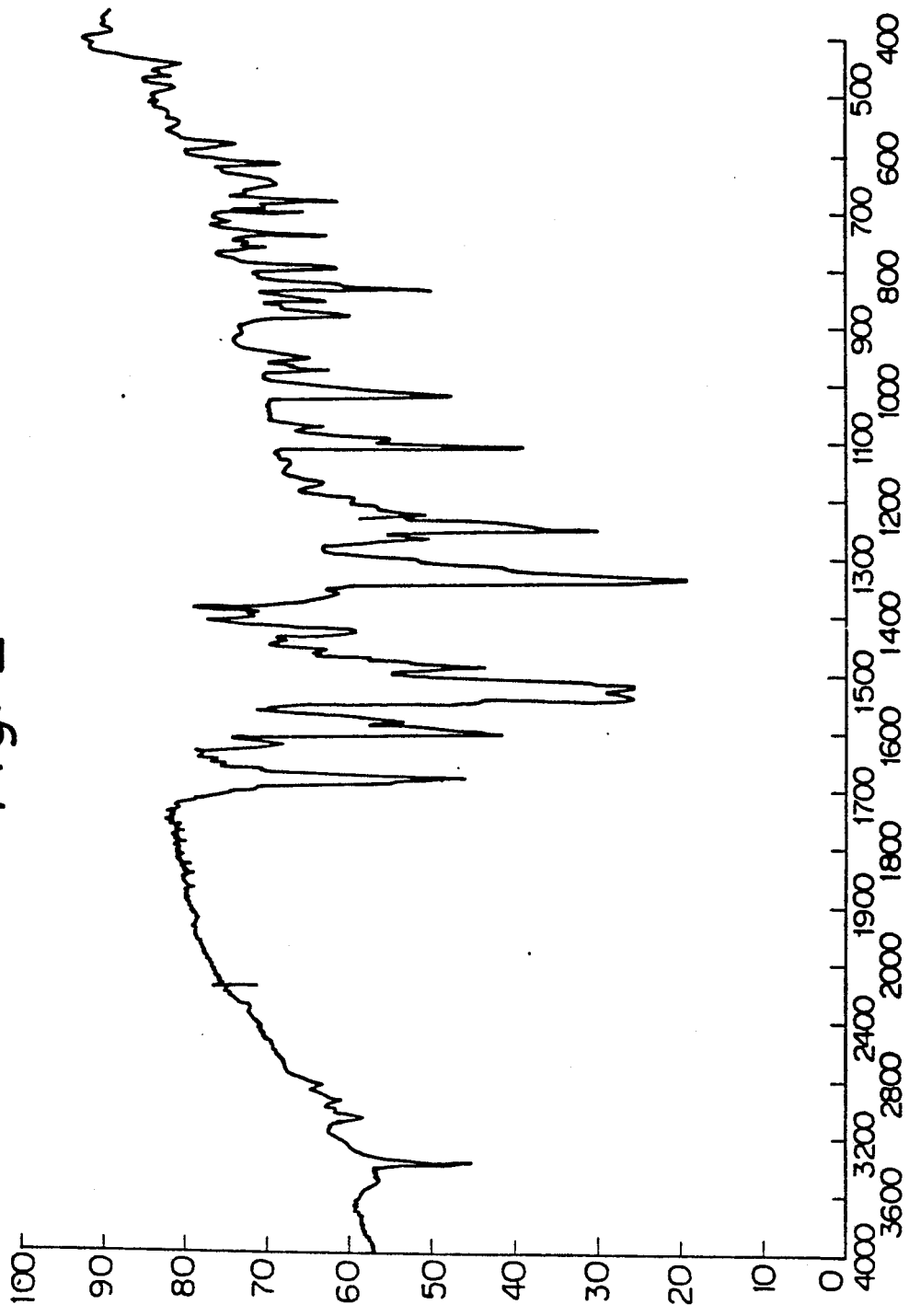

Identification was performed by IR and elementary analysis (see Table 1 and the spectral chart of FIG. 2).

In order to examine the optical nonlinearity and the resistance to laser damage of this compound, the SHG was measured according to the method described in Example 1.

It was found that the MNBA-Br according to the present invention had an SHG 67 times that of urea, and had a high resistance to laser damage. (See Tables 2 and 3).

When the water-solubility of the compound was examined, it was found that MNBA-Br was practically insoluble in water. (See Table 4).

EXAMPLE 3

4'-Nitrobenzylidene-3-chloroacetylamino-4-methoxyaniline (MNBA-Cl)

(Synthesis 1)

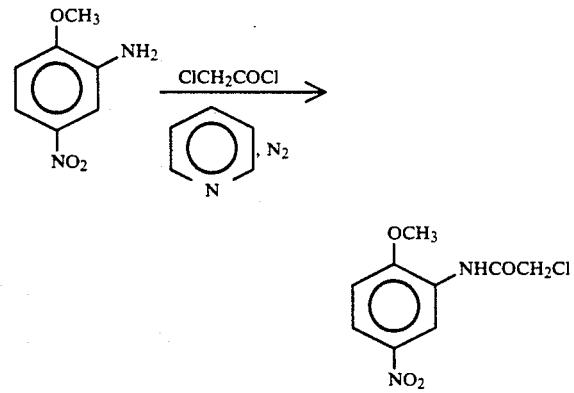

Following generally Synthesis 1 in Example 2, except that 11.3 g of chloroacetyl chloride was used, light yellow 2-chloroacetylamino-4-nitroanisole was prepared in the yield of 87.6% (21.5 g).

(Synthesis 2)

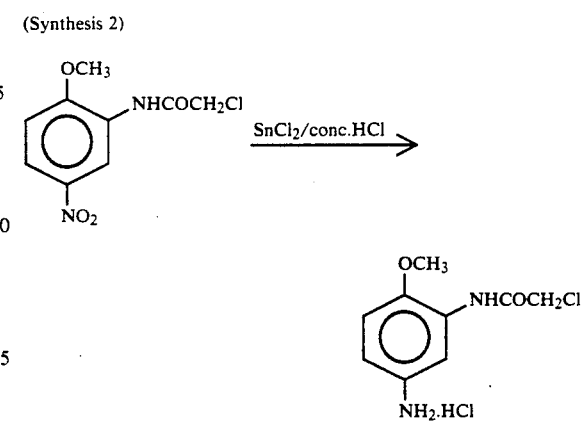

Following generally Synthesis 2 in the Example 2, except that 12.3 g (50 millimoles) of 2-chloroacetylamino-4-nitroanisole was used, 3-chloroacetylamino-4-methoxyaniline hydrochloride was prepared in the yield of 47.7% (6.0 g).

(Synthesis 3)

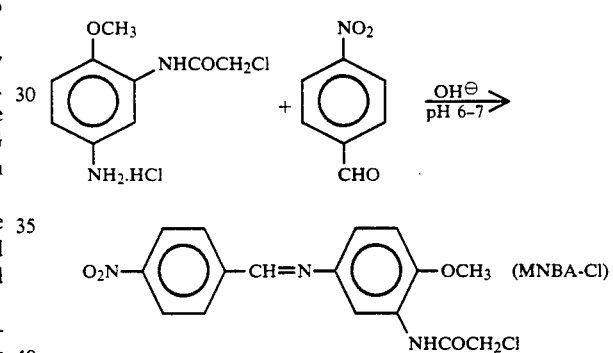

Following generally Synthesis 3 in Example 2, except that 2.51 g (10 millimoles) of 3-chloroacetylamino-4-methoxyaniline hydrochloride was used, yellow 4'-nitrobenzylidene-3-chloroacetylamino-4- methoxy aniline (MNBA-Cl) was prepared in the yield of 42.0% (1.46 g). The melting point was 182 to 185° C.

Figure 3:
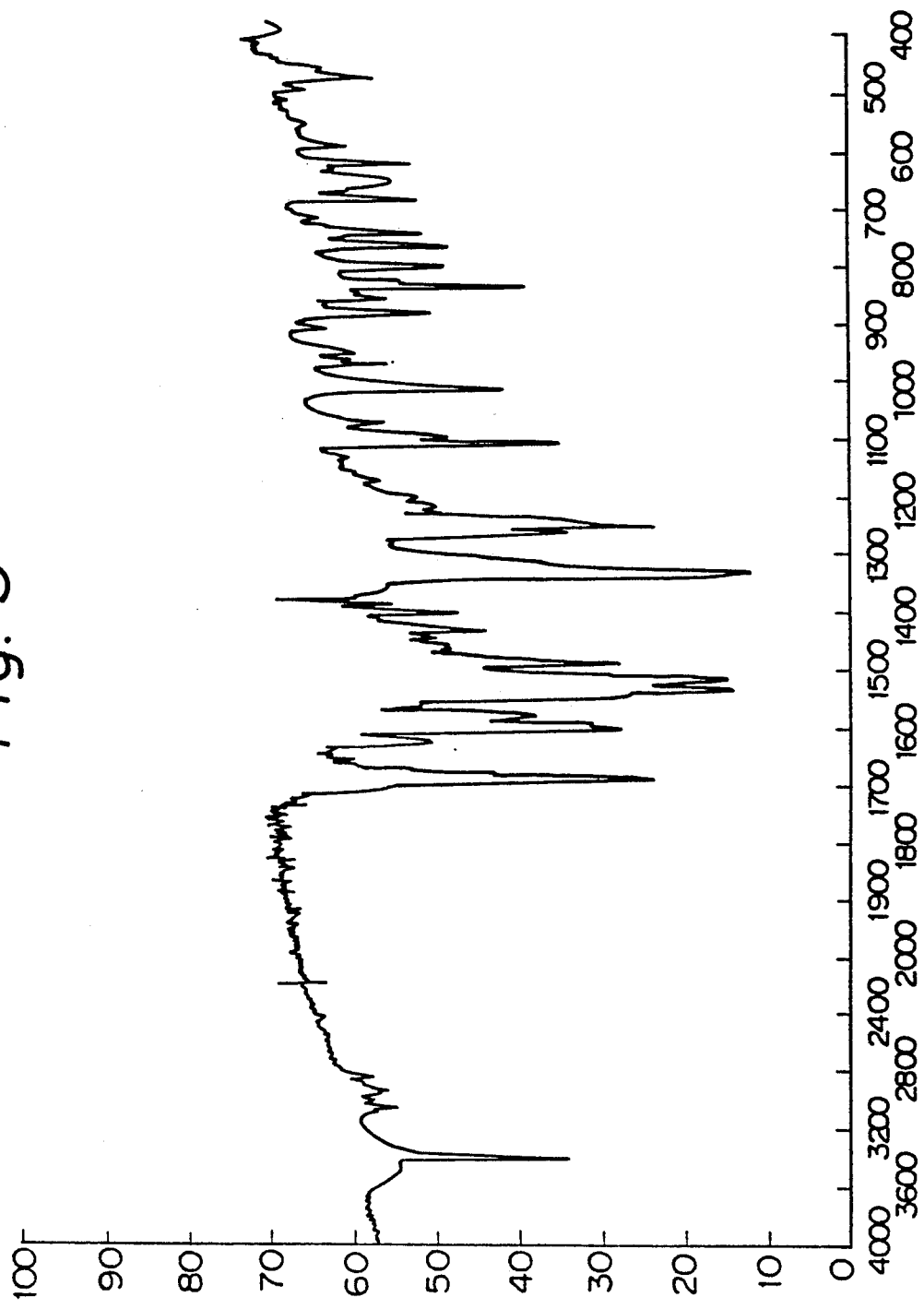

Identification was performed by IR and elementary analysis,(see Table 1 and the spectral chart of FIG. 3).

In order to examine the optical nonlinearity and the resistance to laser damage of this compound, the SHG was measured according to the method described in Example 1.

It was found that the MNBA-Cl according to the present invention had an SHG 33 times that of urea, and had a high resistance to laser damage (See Table 2 and 3).

When the water-solubility of the compound was examined, it was found that MNBA-Cl was practically insoluble in water. (See Table 4).

EXAMPLE 4

4'-Nitrobenzylidene-3-chloro-4-hydroxyaniline (HNBC)

(Synthesis 1)

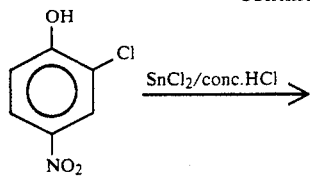

In about 60 cc of concentrated hydrochloric acid was dissolved 40.4 g (180 millimoles) of tin chloride dihydrate, 10.4 g (60 millimoles) of 2-chloro-4-nitrophenol was added to the solution with violent stirring, and the mixture was stirred at about 100° C.

At this point, the yellow color of the reaction solution was faded to a yellowish white color. After about 5 hours, the reaction was stopped and the reaction solution was cooled. The intended aniline hydrochloride and the unreacted compound were precipitated, and the precipitate was collected, washed with acetone, and vacuum-dried to obtain 4.13 g of the intended compound. The yield was 38.2%.

(Synthesis 2)

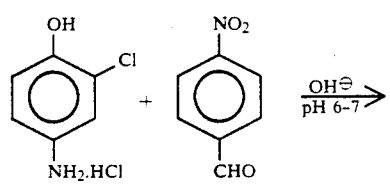

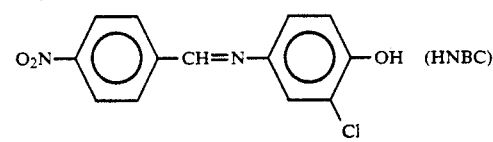

A 200 ml three-necked flask equipped with a reflux condenser and a magnetic stirrer was charged with 2.16 g (12 millimoles) of 3-chloro-4-hydroxyaniline hydrochloride and 1.56 g (10 millimoles) of p-nitrobenzaldehyde, and the mixture was stirred at room temperature for about 10 minutes by using about 60 ml of ethanol/water (2/1) as a reaction solvent.

Then, an aqueous solution of sodium hydroxide was gradually added to the reaction solution until the pH became between 6 and 7, whereby the color of the reaction solution was changed to a red color. The reaction solution was then stirred at room temperature for about 3 hours.

After confirmation of completion of the reaction by thin layer chromatography using chloroform as the developing solvent, stirring was stopped, and the precipitated crude product was collected and washed with cold ethanol.

The so-obtained yellow crude product was dissolved in acetone, and insoluble substances were removed, and the solvent was removed by a rotary evaporator to obtain a yellow crude crystal.

Recrystallization of the crude crystal from an acetone/benzene (½) mixed solvent gave a yellow crystal. The crystal was collected and vacuum-dried to obtain 1.55 g of the intended compound (HNBC). The yield was 62.2%. The melting point was 196.5° to 197.5° C.

Figure 4:
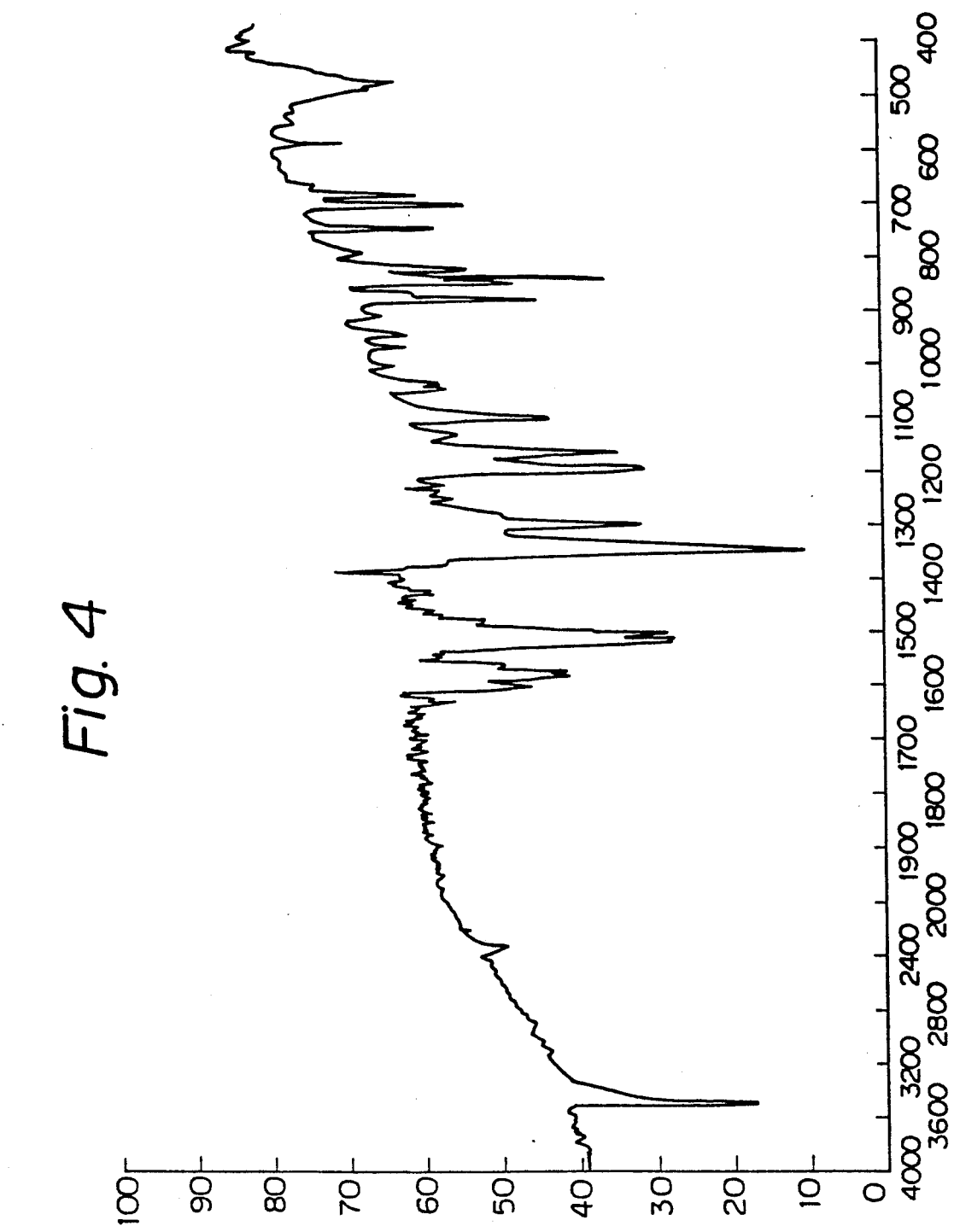

Identification was performed by IR and elementary analysis (See Table 1 and the spectal chart of FIG. 4).

In order to examine the optical nonlinearity and the resistance to laser damage of this compound, the SHG was measured according to the method described in Example 1.

It was found that the HNBC according to the present invention had an SHG 35 times that of urea, and had a high resistance to laser damage (See Tables 2 and 3).

When the water-solubility was examined, it was found that the HNBC according to the present invention was practically insoluble in water. (See Table 4).

EXAMPLE 5

2'-Chloro-4'-nitrobenzylidene-4-methoxyaniline (MNBC)

(Synthesis 1)

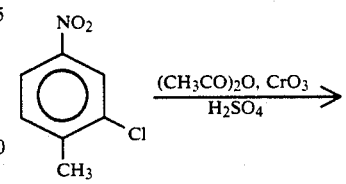

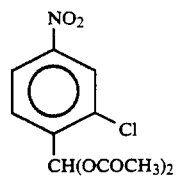

A 1000 ml three-necked flask equipped with a reflux condenser and a magnetic stirrer, which was cooled by ice water, was charged with 230 ml of acetic acid, 230 ml of acetic anhydride and 25 g (146 millimoles) of 2-chloro-4-nitrotoluene, and the mixture was stirred. Then, 34.5 ml of concentrated sulfuric acid was gradually added to the solution.

Then, 40.6 g (406 millimoles) of chromium trioxide was added little by little to the solution carefully so that the temperature of the reaction solution did not exceed 10° C. After completion of the addition, the mixture was further stirred for 1 hour, and the reaction liquid was poured into about 1000 ml of ice water and ice water was further added until the total volume became about 3000 ml, whereby a solid of 2-chloro-4-nitrobenzal diacetate was precipitated. The solid was recovered by filtration, washed with cold water, and dried to obtain 16.8 g of the intended compound. The yield was 40.0%.

(Synthesis 2)

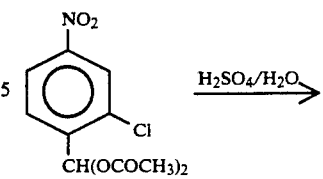

-continued

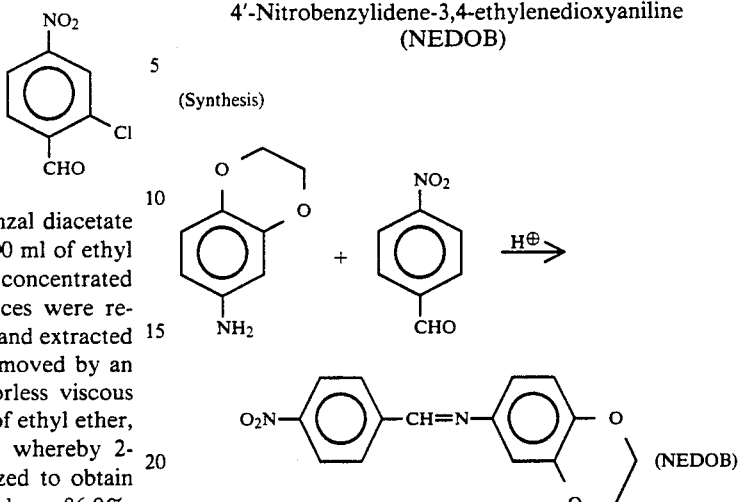

The whole amount of 2-chloro-nitrobenzal diacetate obtained was heated and refluxed with 100 ml of ethyl alcohol, 100 ml of water and 10 ml of concentrated sulfuric acid, and then insoluble substances were removed. The solution was poured onto ice and extracted with chloroform, and the solvent was removed by an evaporator to obtain a substantially colorless viscous liquid. The liquid was dissolved in 10 ml of ethyl ether, and the solution was allowed to stand, whereby 2-chloro-4-nitrobenzaldehyde was crystallized to obtain 9.32 g of the intended compound. The yield was 86.0%.

(Synthesis 3)

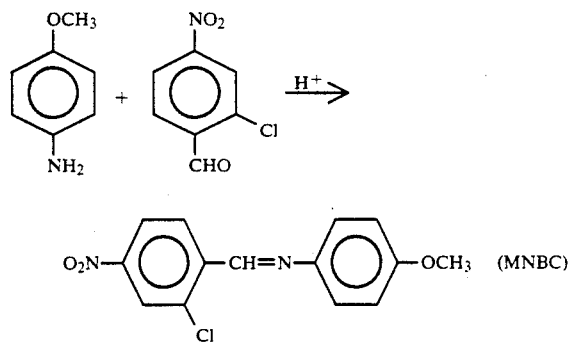

Figure 5:
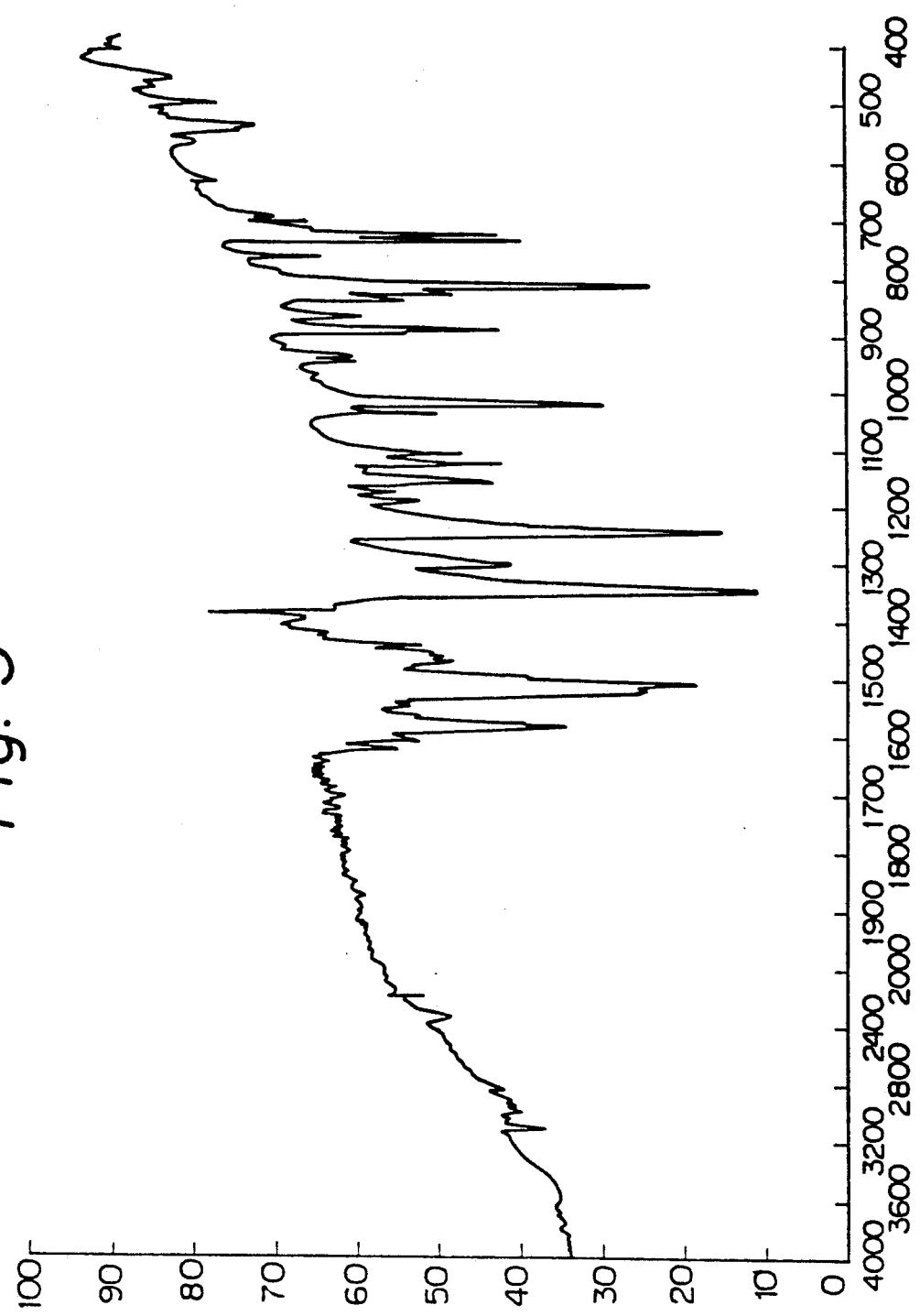

A 200 ml three-necked flask equipped with a reflux condenser and a magnetic stirrer was charged with 9.3 g (50 millimoles) of 2-chloro-4-nitrobenzaldehyde, 6.15 g (50 millimoles) of 4-methoxyaniline (p-anisidine), 0.1 g of p-toluenesulfonic acid and 50 ml of ethyl alcohol, and the mixture was stirred. A yellowish orange precipitate was gradually formed in the reaction solution. The reaction was conducted at the reflux temperature for about 5 hours, and the reaction solution was cooled. The crude crystal of intended 2'-chloro-4'-nitrobenzylidene-4-methoxyaniline (MNBC) became precipitated. The crude crystal was collected, washed with cold ethanol and vacuum-dried. Recrystallization from ethanol produced 6.32 g of the intended compound. The yield was 43.5%. The melting point was 108° to 110° C. Identification was performed by IR and elementary analysis (See Table 1 and the spectral chart of FIG. 5).

In order to examine the optical nonlinearity and the resistance to laser damage, the SHG was measured according to the method described in Example 1.

It was found that the MNBC according to the present invention had an SHG 13 times that of urea, and had a high resistance to laser damage (See Tables 2 and 3).

When the water-solubility was examined, it was found that the MNBC according to the present invention was practically insoluble in water. (See Table 4).

EXAMPLE 6

4'-Nitrobenzylidene-3,4-ethylenedioxyaniline (NEDOB)

(Synthesis)

A 200 ml three-necked flask equipped with a reflux condenser and a magnetic stirrer was charged with 7.55 g (50 millimoles) of 3,4-ethylenedioxyaniline and 7.55 g (50 millimoles) of p-nitrobenzaldehyde, and the mixture was stirred at room temperature for about 10 minutes by using about 100 ml of ethanol as a reaction solvent.

Then, abut 17 g (1 millimole) of p-toluenene-sulfonic acid was added as the catalyst and stirring was continued at room temperature for abut 3 hours and at reflux temperature for about half an hour to complete the reaction. After confirmation of completion of the reaction by thin layer chromatography using chloroform as the developing solvent, stirring was stopped and the reaction mixture was cooled with ice water.

The yellow precipitated crude product was collected and washed with cold ethanol.

The yellow crude crystal obtained was recrystallized from cyclohexane to obtain a yellow needle crystal, and the crystal was collected and vacuum-dried to obtain 12.2 g of the intended compound (NEDOB). The yield was 85.9%. The melting point was 169.5° to 171° C.

Figure 6:
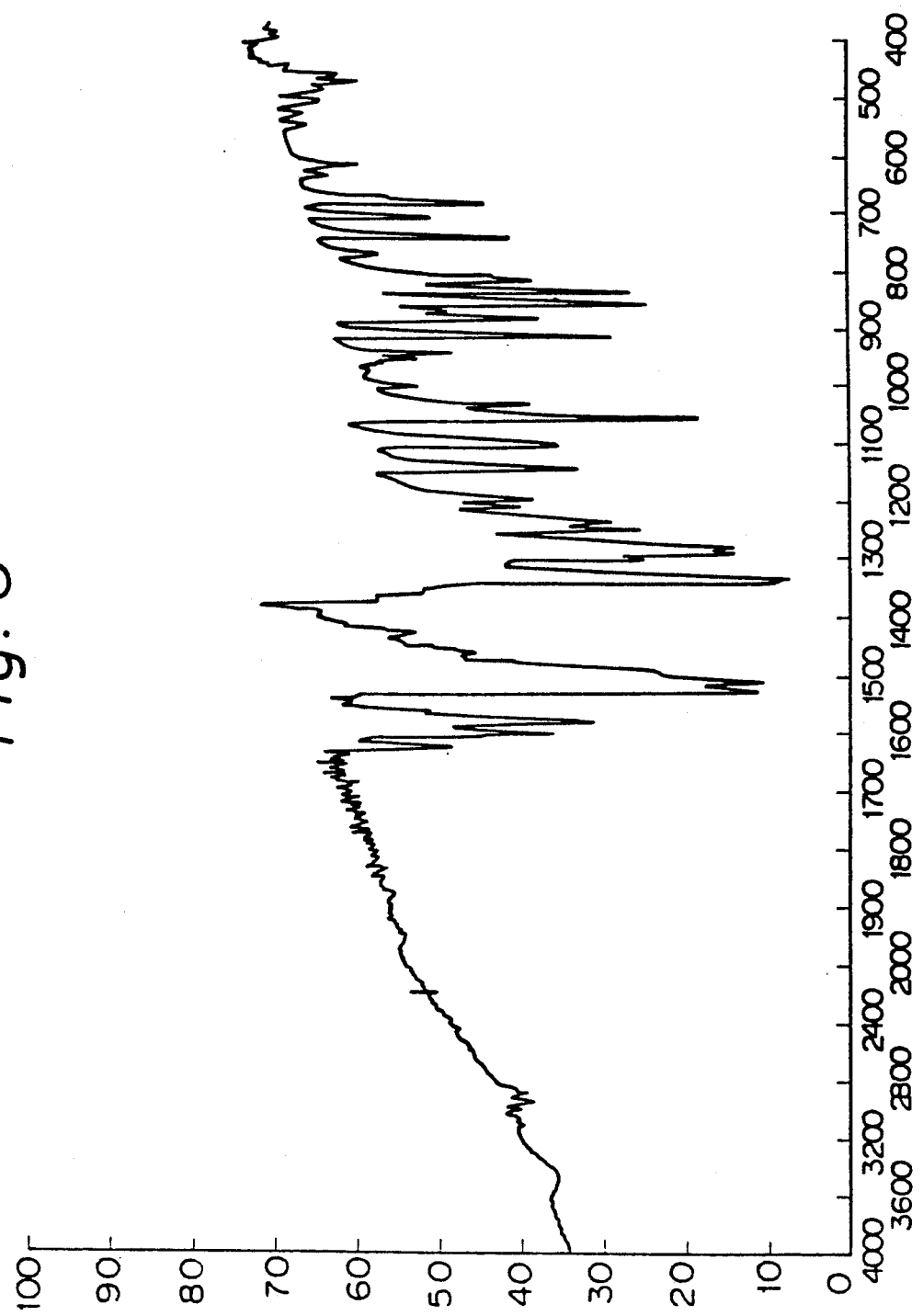

Identification was performed by IR and elementary analysis (See Table 1 and the spectral chart of FIG. 6).

In order to examine the optical nonlinearity and the resistance to laser damage of this compound, the SHG was measured according to the method described in Example 1.

It was found that the NEDOB according to the present invention had an SHG 130 times that of urea, and had a high resistance to laser damage (see Table 2 and 3).

When the water-solubility of the compound was examined, it was found that NEDOB was practically insoluble in water. (See Table 4).

COMPARATIVE EXAMPLE 1

2-Methyl-4-nitroaniline (MNA)

Commercially available MNA was recrystallized from benzene/methanol (3/1), and with respect to the obtained yellow crystal, the optical nonlinearity (SHG) and the resistance to laser damage were evaluated according to the measurement method described in Example 1.

It was found that the MNA had an SHG 50 times that of urea, but the MNA was promptly degraded by irradiation of the laser beam having a repetition frequency of 10 kHz (See Tables 2 and 3).

When the water-solubility was examined, it was found that MNA was soluble in water. (See Table 4).

COMPARATIVE EXAMPLE 2

2-Acetylamino-4-nitro-N,N-dimethylaniline (DAN)

Synthesis was carried out according to the following synthetic process.

(Synthesis 1)

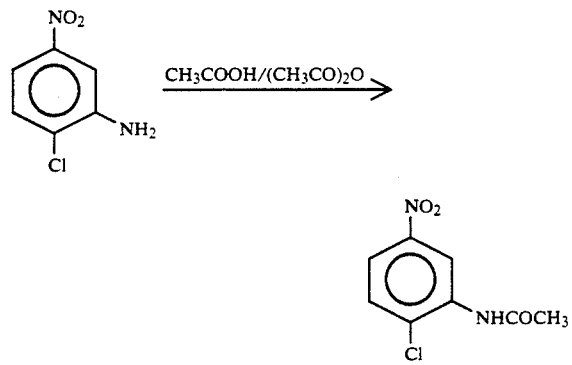

A 200 ml three-necked flask equipped with a reflux condenser and a magnetic stirrer was charged with about ml of acetic acid/acetic anhydride (1/1) and 8.63 g (50 millimoles) of 2-chloro-5-nitroaniline, and the mixture was stirred at room temperature.

After about 5 hours, a crude crystal was precipitated and the whitened reaction solution was poured into cold water. The white crude crystal was collected and the crystal was heated and dried in vacuum to obtain 9.84 g of the intended compound. The yield was 91.7%.

(Synthesis 2)

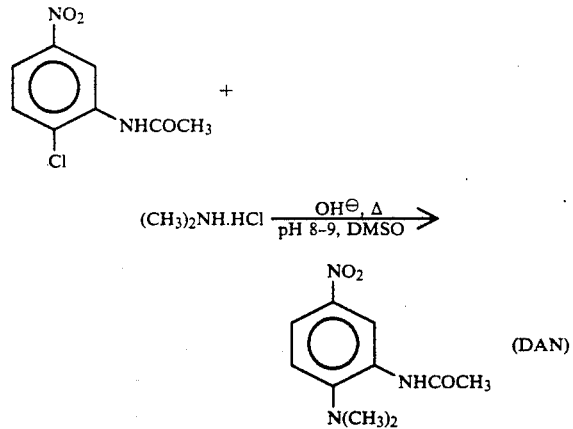

A 200 ml three-necked flask equipped with a reflux condenser and a magnetic stirrer was charged with 0.81 g of N,N-dimethylamine hydrochloride, and about 8 ml of dimethylsulfoxide, and the mixture was stirred at room temperature for about 5 minutes.

Then, 4.29 g (20 millimoles) of 3-acetylamino-4-chloronitrobenzene was gradually added to the reaction mixture. Then, an aqueous solution of Sodium hydroxide was gradually added to the reaction solution until the pH value became between 8 and 9, whereby the color of the reaction solution was changed to a yellowish orange color. Stirring was conducted at 50° C. for about 3 hours.

After confirmation of completion of the reaction by thin layer chromatography using chloroform as the developing solvent, the reaction solution was poured into cold water.

The precipitated brownish yellow crude crystal was collected, and dried in vacuum with heating.

Recrystallization of the crude crystal from acetone/ethanol (4/1) gave 3.08 g of a yellow needle crystal of the intended compound (DAN). The yield was 68.9%. The melting point was 167.5° to 168° C.

Figure 7:
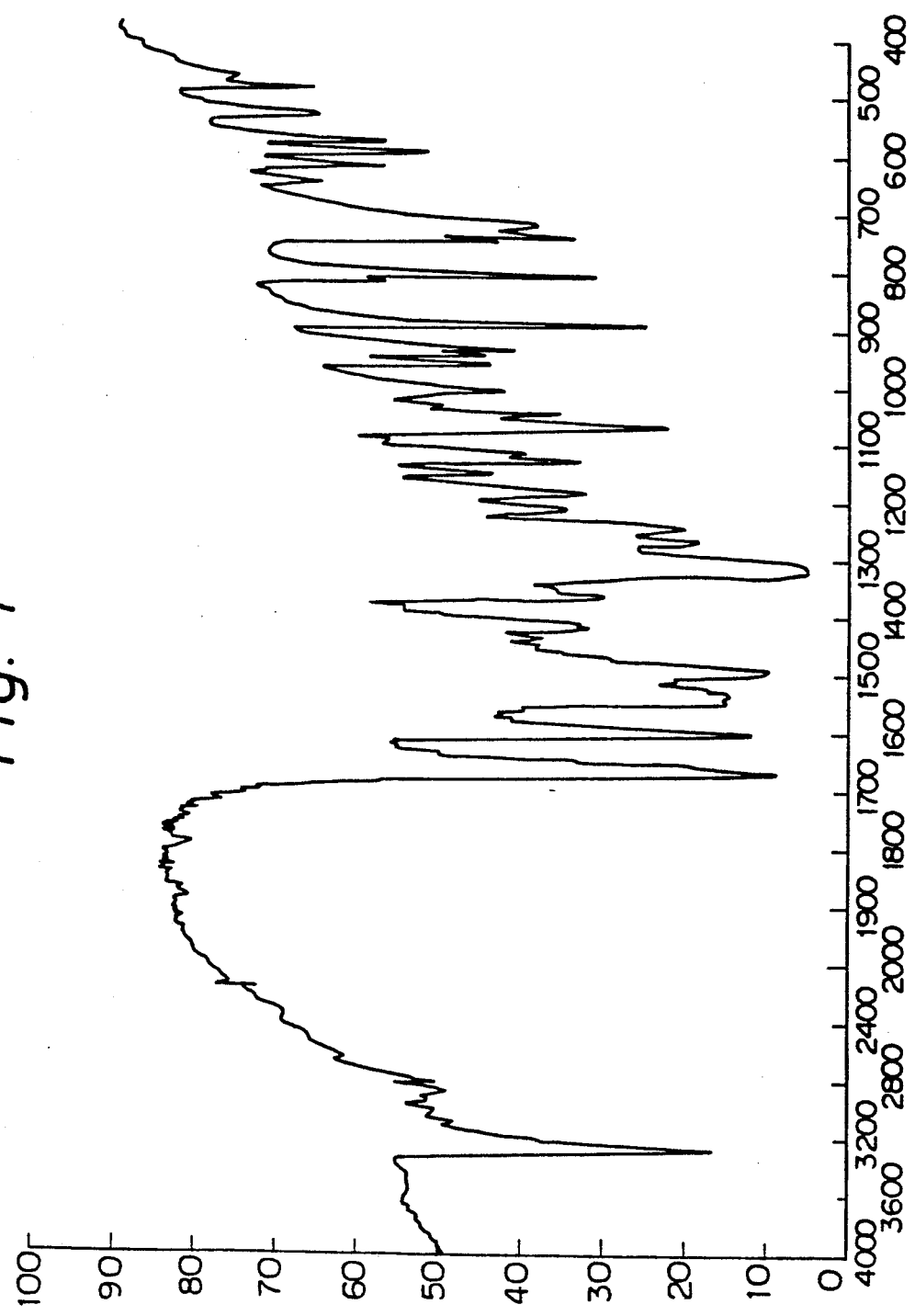

Identification was performed by IR and elementary analysis (See Table 1 and the spectral chart of FIG. 7).

With respect to the obtained yellow crystal, the optical nonlinearity (SHG) and the resistance to laser damage were evaluated according to the method described in Example 1.

It was found that the DAN had an SHG 120 times that of urea, but the DAN was promptly degraded by irradiation of the laser beam having a repetition frequency of 10 kHz (See Tables 2 and 3).

When the water-solubility was examined, it was found that the DAN was soluble in water. (See Table 4).

COMPARATIVE EXAMPLE 3

N-[2-(5-Nitro)-pyridyl,]-(L)-prolinol (PNP)

The compound was prepared according to the process disclosed in the literature reference [R. J. Twieg and C. H. Dirk, J. Chem. Phys., 85(6), 3537 (1986)], and the optical nonlinearity and the resistance to laser damage were evaluated according to the method described in Example 1.

The PNP had an SHG 130 times that of urea, but the PNP was promptly degraded by irradiation of the laser beam having a repetition frequency of 10 kHz, (See Tables 2 and 3).

When the water-solubility was examined, it was found that PNP was extremely soluble in water. (See Table 4).

COMPARATIVE EXAMPLE 4

N-(4-Nitrophenyl)-(L)-prolinol (NPP)

The compound was prepared according to the process disclosed in the literature reference [J. Zyss et al., J. Chem. Phys., 81(9), 4160 (1984)], and the optical nonlinearity (SHG) and the resistance to laser damage were evaluated according to the method described in Example 1.

It was found that the PNP had an SHG 130 times that of urea, but the PNP was promptly degraded by irradiation of the laser beam having a repetition frequency of kHz (See Tables 2 and 3).

When the water-solubility was examined, it was found that the NPP was soluble in water. (See Table 4).

COMPARATIVE EXAMPLE 5

4'-Nitrobenzylidene-4-methoxyaniline (MNB)

(Synthesis)

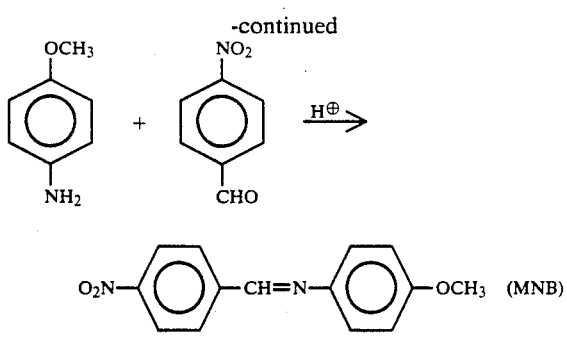

A 200 ml three-necked flask equipped with a reflux condenser and a magnetic stirrer was charged with 2.46 g (20 millimoles) of p-anisidine (4-methoxyaniline) and 3.02 g (20 millimoles) of p-nitrobenzaldehyde, and the mixture was stirred at room temperature for about 10 minutes by using about 50 ml of ethanol as a reaction solvent.

Then, about 17 mg (1 millimole) of p-toluenesulfonic acid was added as the catalyst and stirring was further conducted at room temperature for about 3 hours to accomplish crystallization of the brownish yellow intended compound.

After confirmation of completion of the reaction by thin layer chromatography using chloroform as the developing solvent, stirring was stopped. The precipitated crude product was collected and washed with cold ethanol.

The obtained brownish yellow crude crystal was recrystallized from an acetone/benzene (1/1) mixed solvent to obtain a yellow crystal, and the crystal was collected and vacuum-dried to obtain 3.95 g of the intended compound (MNB). The yield was 77.2%. The melting point was 135.5° to 136.0° C.

Figure 8:
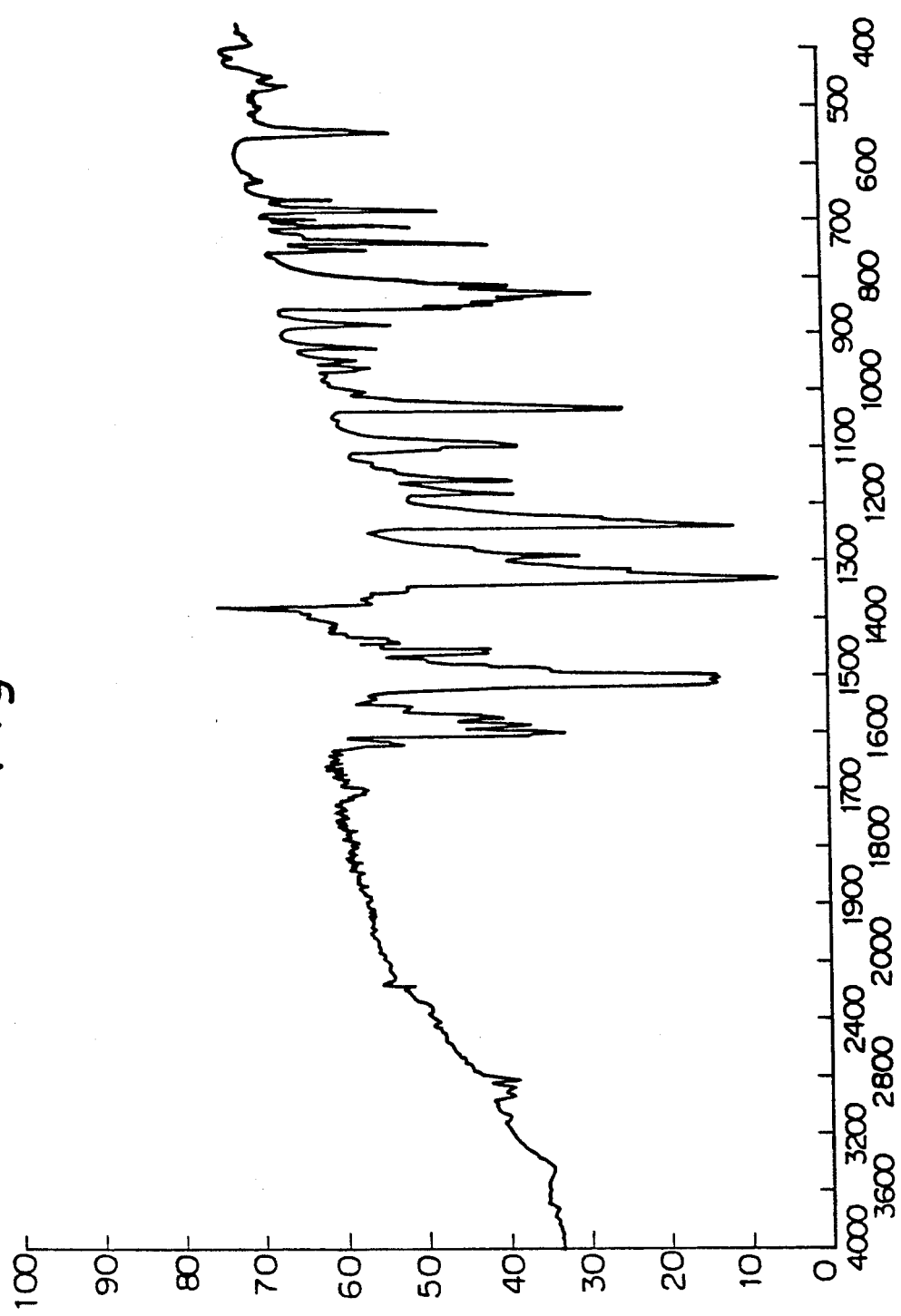

Identification was performed by IR and elementary analysis (see Table 1 and the spectral chart of FIG. 8).

With respect to the obtained yellow crystal, the optical nonlinearity (SHG) and the resistance to laser damage were evaluated according to the measurement method described in Example 1.

It was found that the MNB manifested only an SHG 0.2 times that of urea, and because of a low SHG value an evaluation of the resistance to laser damage was impossible. (See Tables 2 and 3).

When the water-solubility was examined, it was found that the MNB was completely insoluble in water. (See Table 4).

COMPARATIVE EXAMPLE 6

4'-Nitrobenzylidene-4-hydroxyaniline (HNB)

(Synthesis)

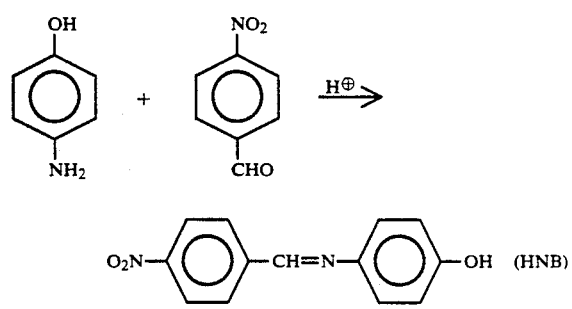

A 200 ml three-flasked equipped with a reflux condenser and a magnetic stirrer was charged with 2.18 g (20 millimoles) of p-aminophenol and 3.12 g (20 millimoles) of p-nitrobenzaldehyde, and the mixture was stirred at room temperature for about 10 minutes by using about 50 ml of ethanol as a reaction solvent. Then, about 17 mg (1 millimole) of p-toluenesulfonic acid was added as the catalyst, and stirring was conducted at room temperature for about 3 hours. At this point, the intended orange compound was crystallized.

After confirmation of completion of the reaction by the thin layer chromatography using chloroform as the developing solvent, stirring was stopped. The precipitated crude product was collected and washed with cold ethanol.

The obtained orange crude crystal was recrystallized from ethanol to obtain an orange crystal. The crystal was collected and vacuum-dried to obtain 3.13 g of the intended compound (HNB). The yield was 64.7%. The melting point was 172° to 173° C.

Figure 9:
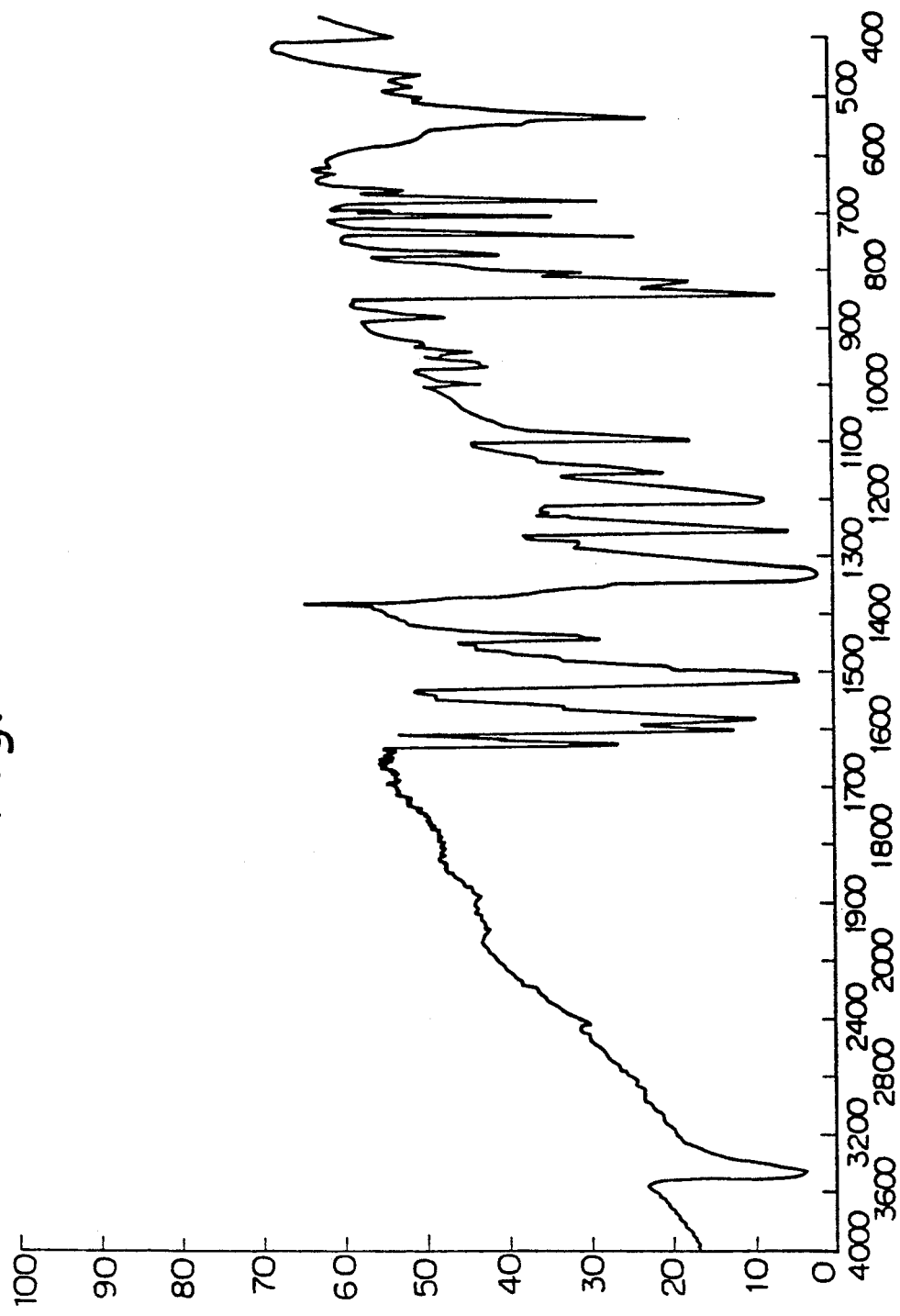

Identification was performed by IR and elementary analysis. (See Table 1 and the spectral chart of FIG. 9).

Then, with respect to the obtained orange crystal, the optical nonlinearity (SHG) and the resistance to laser damage were evaluated according to the measurement method described in Example 1.

It was found that the HNB was SHG-inactive and an evaluation of the resistance to laser damage was impossible. (See Tables 2 and 3).

When the water-solubility was examined it was found that the HNB was insoluble in water. (See Table 4).

TABLE 1

| | Results of Elementary Analysis (C, H and N) | | | | | |
|---|---|---|---|---|---|---|
| | | Calculated Values | | | Found Values | | |
| | Compound | C | H | N | C | H | N |
| Example 1 | MNBA | 61.3 | 4.8 | 13.4 | 61.2 | 4.8 | 13.3 |
| Example 2 | MNBA—Br | 49.0 | 3.6 | 10.7 | 49.1 | 3.7 | 10.8 |
| Example 3 | MNBA—Cl | 55.3 | 4.1 | 12.1 | 55.2 | 4.0 | 12.2 |
| Example 4 | HNBC | 56.4 | 3.3 | 10.1 | 56.5 | 3.3 | 10.3 |
| Example 5 | MNBC | 57.8 | 3.8 | 9.6 | 57.7 | 3.8 | 9.7 |
| Example 6 | NEDOB | 63.4 | 4.3 | 9.9 | 63.3 | 4.2 | 10.0 |
| Comparative Example 1 | DAN | 53.8 | 5.9 | 18.8 | 54.0 | 5.8 | 18.7 |
| Comparative Example 5 | MNB | 65.6 | 4.7 | 10.9 | 65.7 | 4.6 | 11.0 |
| Comparative Example 6 | HNB | 64.5 | 4.2 | 11.6 | 64.7 | 4.1 | 11.5 |

TABLE 2

| SHG of Organic Nonlinear Optical Compound ($\lambda = 1.06 \mu m$) | | |
|---|---|---|
| | Compound | SHG (urea ratio) |
| Example 1 | MNBA | 233 |
| Example 2 | MNBA—Br | 67 |
| Example 3 | MNBA—Cl | 33 |
| Example 4 | HNBC | 35 |
| Example 5 | MNBC | 13 |
| Example 6 | NEDOB | 130 |
| Comparative Example 1 | MNA | 50 |
| Comparative Example 2 | DAN | 120 |
| Comparative Example 3 | PNP | 130 |
| Comparative Example 4 | NPP | 110 |
| Comparative Example 5 | MNB | 0.2 |
| Comparative | HNB | 0.0 |

TABLE 2-continued

SHG of Organic Nonlinear
Optical Compound ($\lambda = 1.06$ μm)

| Compound | SHG (urea ratio) |
|---|---|
| Example 6 | |

TABLE 3

Results of Evaluation of Resistance to Laser Damage
in Organic Nonlinear Optical Compound

| | Compound | Degradation Rate under Condition 1 | Degradation Rate under Condition 2 |
|---|---|---|---|
| Example 1 | MNBA | Slow | Slow |
| Example 2 | MNBA—Br | None | None |
| Example 3 | MNBA—Cl | None | None |
| Example 4 | HNBC | Fast | None |
| Example 5 | MNBC | — | — |
| Example 6 | NEDOB | Slow | None |
| Comparative Example 1 | MNA | Fast | Moderately |
| Comparative Example 2 | DAN | Fast | Moderately |
| Comparative Example 3 | PNP | Very fast | Fast |
| Comparative Example 4 | NPP | Fast | Fast |
| Comparative Example 5 | MNB | — | |
| Comparative Example 6 | HNB | — | — |

Note
Condition 1: pulse width of 200 nsec, repetition frequency of 10 kHz, peak power density of 9.1 MW/cm²
Condition 2: continuous oscillation, average power density of 16 kW/cm²

TABLE 4

Water-Solubilities of Organic Nonlinear
Optical Compounds

| Compound | | Water-Solubility (g/100 ml) |
|---|---|---|
| Example 1 | MNBA | — |
| Example 2 | MNBA—Br | — |
| Example 3 | MNBA—Cl | — |
| Example 4 | HNBC | — |
| Example 5 | MNBC | — |
| Example 6 | NEDOB | — |
| Comparative Example 1 | MNA | $1.0 \times 10^{-2}$ |
| Comparative Example 2 | DAN | $2.5 \times 10^{-2}$ |
| Comparative Example 3 | PNP | $2.0 \times 10^{-1}$ |
| Comparative Example 4 | NPP | $2.2 \times 10^{-2}$ |
| Comparative Example 5 | MNB | — |
| Comparative Example 6 | HNB | — |

Note
—: not dissolved: solubility at 25° C. lower than $1.0 \times 10^{-4}$ g/100 ml.

We claim:

1. A non-centrosymmetric crystal of a benzylidene-aniline derivative which has a second-order optical nonlinearity of the formula 1,

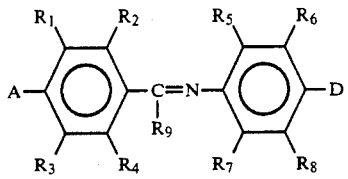

said benzylidene-aniline derivative having (1) an electron-donating substituent D of a Hammett substituent constant $\sigma p$ of $\sigma p < 0$ at the 4-position, (2) an electron-accepting substituent A of a Hammett substituent constant $\sigma p$ of $\sigma p \geq 0$ at the 4'-position, and (3) substituents $R_1$ through $R_9$, at least one of which is a molecular alignment-regulating substituent that forms hydrogen bonds or causes large steric hindrance which is a halogen atom, wherein said crystal has a second-order optical nonlinearity at least 10 times that of urea.

2. A non-centrosymmetric crystal as set forth in claim 1, wherein the benzylidene-aniline derivative is 4'-nitrobenzylidene-3-chloro-4-hydroxyaniline.

3. A non-centrosymmetric crystal of a benzylidene-aniline derivative which has a second-order optical nonlinearity of the formula 1,

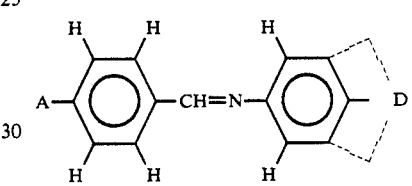

said benzylidene-aniline derivative having (1) a molecular alignment regulating and electron-donating substituent indicated by the linkage between the aromatic ring and D in formula (1) of a Hammett substituent constant $\sigma p < 0$, which is substituent at the 4-position or the 3,4-positions of aniline or at the 3,4,5-positions of aniline, (2) an electron-accepting substituent A of a Hammett substituent constant $\sigma p$ of $\sigma p \geq 0$ at the 4'-position, wherein said crystal has a second-order optical nonlinearity at least 10 times that of urea.

4. A non-centrosymmetric crystal as set forth in claim 3, wherein the water-solubility of said crystal at 25° C. is lower than $1.0 \times 10^{-2}$ g/100 ml.

5. A non-centrosymmetric crystal as set forth in claim 3, wherein the optical nonlinearity is at least 150 times that of urea.

6. A non-centrosymmetric crystal as set forth in claim 3, wherein the electron-donating and molecular alignment-regulating substituent (D) is an alkoxy group —ORE in which R stands for an alkyl group, an allyl group, an aryl group, or an aralkyl group.

7. A non-centrosymmetric crystal as set forth in claim 3, wherein the electron-accepting substituent (A) is a nitro group.

8. A non-centrosymmetric crystal as set forth in claim 3, wherein the benzylidene-aniline derivative is 4'-nitrobenzylidene-3,4-ethylenedioxy-aniline.

9. A non-centrosymmetric crystal as set forth in claim 3, wherein all or a part of hydrogen atoms of the benzylidene-aniline derivative represented by the formula (1) are deuterated.

* * * * *